United States Patent [19]
Takeuchi et al.

[11] Patent Number: 5,585,918
[45] Date of Patent: Dec. 17, 1996

[54] FOREIGN PARTICLE INSPECTING SYSTEM

[75] Inventors: Seiji Takeuchi; Kyoichi Miyazaki; Toshihiko Tsuji, all of Utsunomiya, Japan

[73] Assignee: Canon Kabushiki Kaisha, Tokyo, Japan

[21] Appl. No.: 494,539

[22] Filed: Jun. 26, 1995

[30] Foreign Application Priority Data

Jun. 28, 1994 [JP] Japan .................................. 6-168776

[51] Int. Cl.[6] ................................................ H05B 37/00
[52] U.S. Cl. .......................... 356/237; 356/445; 356/337; 356/345
[58] Field of Search ........................... 356/237, 445, 356/337, 345, 386

[56] References Cited

U.S. PATENT DOCUMENTS

| | | | |
|---|---|---|---|
| 5,041,726 | 8/1991 | Chang et al. | 356/237 |
| 5,270,794 | 12/1993 | Tsuji et al. | 356/371 |
| 5,416,594 | 6/1995 | Gross et al. | 356/237 |
| 5,465,145 | 11/1995 | Nakashige et al. | 356/237 |

Primary Examiner—Georgia Y. Epps
Assistant Examiner—Reginald A. Ratliff
Attorney, Agent, or Firm—Fitzpatrick, Cella, Harper & Scinto

[57] ABSTRACT

An inspecting system includes a light source, an irradiating optical system for irradiating a surface of an object such as a reticle or photomask with light from the light source, a detection optical system for detecting scattered light from the surface of the object, and a light blocking device provided substantially parallel to the surface of the object, the light blocking device having a first light transmitting portion for passing light coming from the light source toward the surface of the object and a second light transmitting portion for passing light coming from an irradiated position on the surface of the object toward the detection optical system.

10 Claims, 8 Drawing Sheets

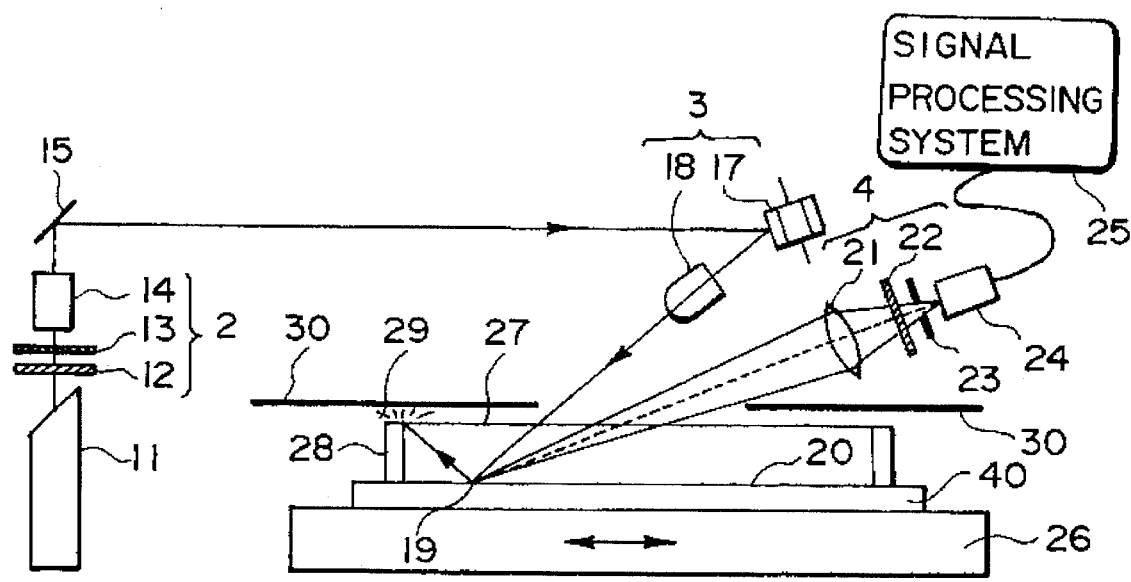
FIG. IA
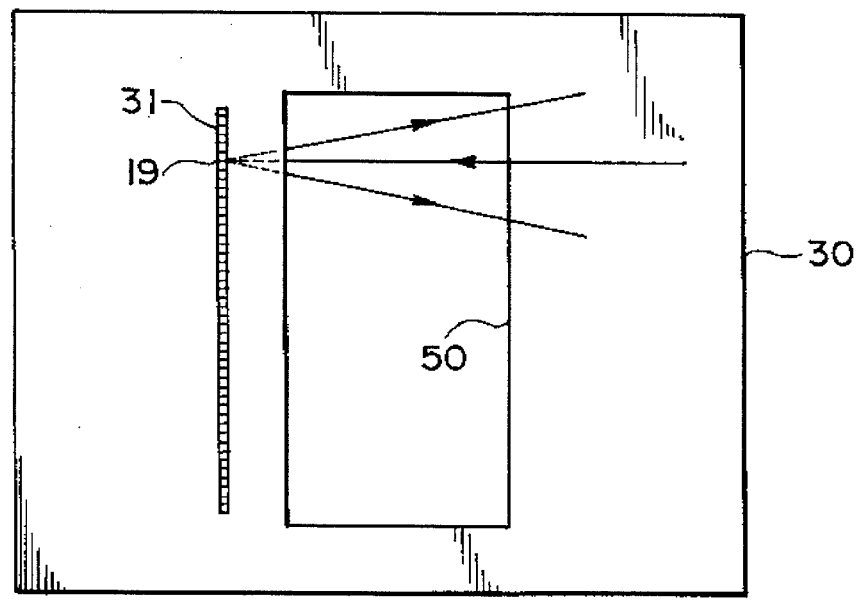
FIG. IB

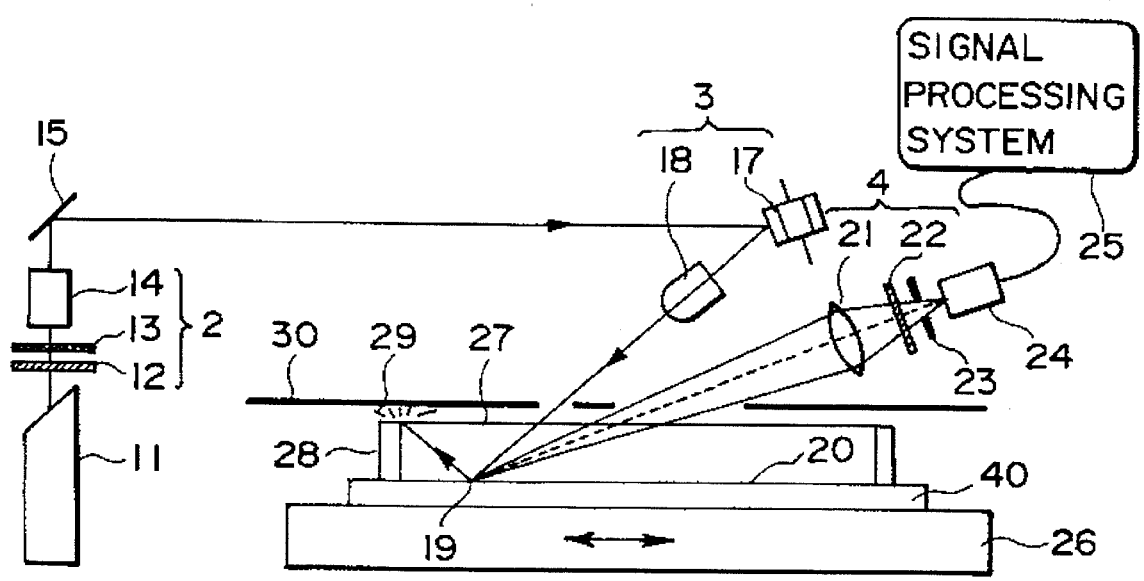
F I G. 3A
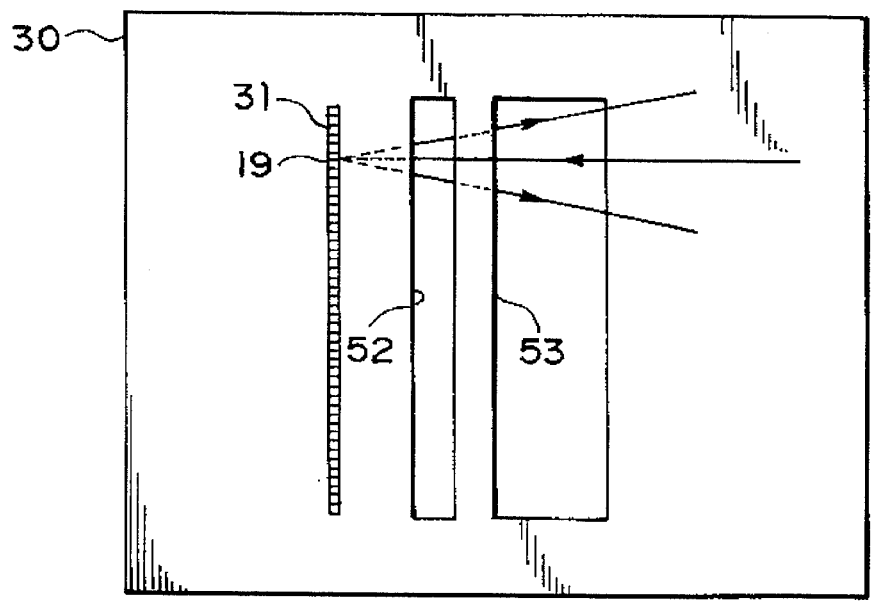
F I G. 3B

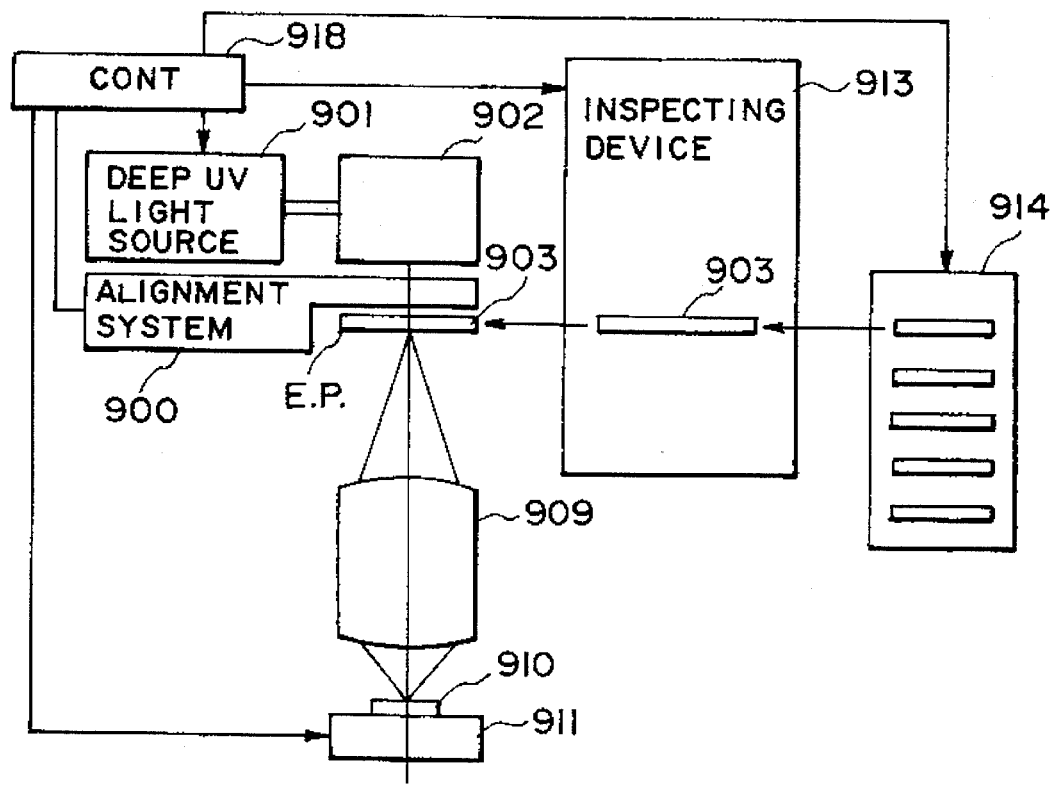
F I G. 7
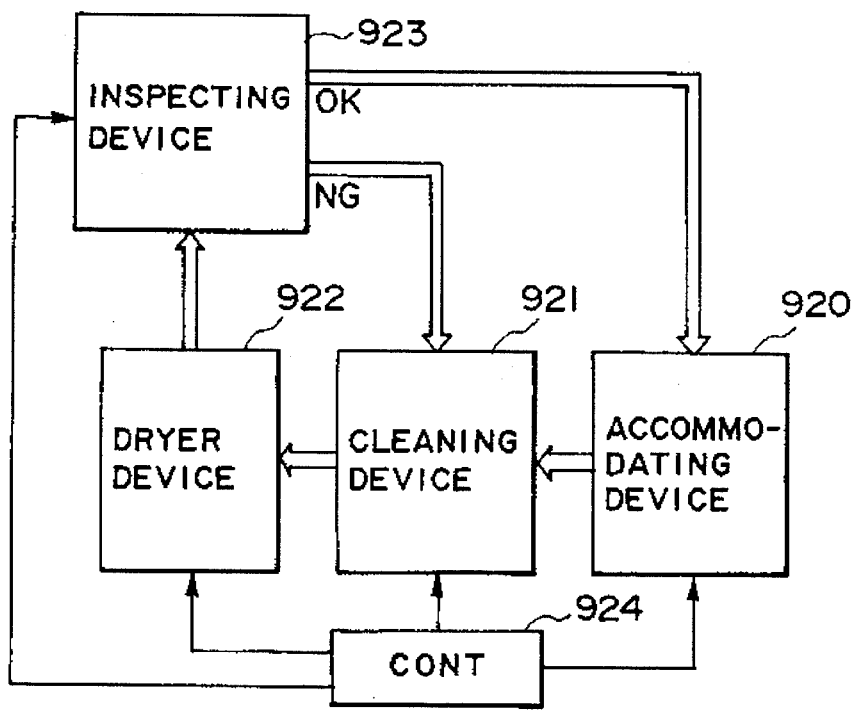
F I G. 8

FOREIGN PARTICLE INSPECTING SYSTEM

FIELD OF THE INVENTION AND RELATED ART

This invention relates generally to a foreign particle inspecting system and, more particularly, to an inspecting system suitably usable for inspection of a foreign particle such as non-transparent dust, for example, if any, adhered to the surface of an original such as a reticle or a photomask on which a circuit pattern for use in the manufacture of semiconductor devices is formed.

Usually, in an IC manufacturing process, a circuit pattern formed on an original such as a reticle or photomask is printed on a resist-coated wafer by using a semiconductor exposure apparatus (stepper or aligner). If, in such a circuit pattern printing process, foreign matter or a particle such as dust is present on the surface of the original, it is also printed on the wafer. This may cause a decreased yield of IC devices.

Particularly when a reticle is used and its circuit pattern is printed on the surface of a wafer repeatedly through the step-and-repeat method, the presence of only a single foreign particle on the surface of the reticle results in repeated printing of that particle on the whole surface of the wafer. This significantly damages the yield of the IC process.

The IC manufacturing processes should include a process of inspecting the presence of a foreign particle on a substrate, and a variety of inspecting methods have been proposed in this respect. Many of these methods utilize the phenomenon that a foreign particle scatters light isotropically.

FIG. 9 is a schematic view of a main portion of an example of a foreign particle inspecting system. This system performs inspection of the presence of a foreign particle by detecting scattered light from the particle. In operation of the inspecting system of FIG. 9, a laser beam from a laser light source 11 is transformed by a collimator optical system 2 into a laser beam suited for particle inspection, and it is directed by a mirror 15 to a scanning optical system 3 which comprises a polygonal mirror 17 and an f-θ lens 18. The laser beam from the scanning optical system 3 is collected as a light spot 19 on the surface 20, to be inspected, of an original 40 on which a circuit pattern is formed. By the scanning optical system 3, the original surface 20 is scanned along a scan line. Simultaneously, by using a scanning stage system 26, the original 40 is moved in a direction substantially perpendicular to the scanning direction of the light spot 19, and the whole original surface 20 is scanned two-dimensionally.

Scattered light from a foreign particle, if any, on the surface 19 being inspected is detected by detecting means 4 which comprises a light receiving lens 21, a filter 22, an aperture member 23 and a photoelectric detector 24, being disposed backwardly or sidewardly with respect to the direction of projection of the laser beam.

As regards the disposition and orientation of this detecting means 4, since, in response to irradiation of the surface 20 with the laser beam, a scattered light is produced by a circuit pattern, for example, which light has a particular diffraction direction or directions, disposition of the detecting means 4 is so selected that it does not receive such diffractively scattered light.

If there is no foreign particle within the range of the light spot 19, in this inspecting system, no scattered light is detected. If there is a foreign particle on the surface 19 to be inspected, scattered light is produced by such a particle isotropically. The thus produced scattered light is detected by the detecting means 4. A detection signal produced thereby is processed by a signal processing system 25, by which the presence/absence of a particle on the surface 19 and/or the size of that particle is inspected.

SUMMARY OF THE INVENTION

In such a foreign particle inspecting system, however, there is a possibility that: light passing through the original 40 or light reflected thereby is reflected by a side face of the original 40 or by a pellicle frame 28, for example, to produce unwanted scattered light which in turn is received by the detecting means. This is a noise component to the detection signal and, in some cases, it causes erroneous detection of a particle.

It is an object of the present invention to provide an improved inspecting system capable of detecting a small foreign particle on a surface to be inspected, very precisely, which particle might not be detected through inspecting systems having been proposed.

In accordance with an aspect of the present invention, a suitable light blocking means is provided to block unwanted scattered light which is produced, during the inspecting process, from any portion off the scan line of a light spot.

These and other objects, features and advantages of the present invention will become more apparent upon a consideration of the following description of the preferred embodiments of the present invention taken in conjunction with the accompanying drawings.

BRIEF DESCRIPTION OF THE DRAWINGS

FIG. 1A is a schematic and side view of a main portion of a foreign particle inspecting system according to a first embodiment of the present invention.

FIG. 1B is a top plan view of a light blocking plate used in the inspecting system of the FIG. 1A embodiment.

FIG. 3A is a schematic and side view of a main portion of a foreign particle inspecting system according to a second embodiment of the present invention.

FIG. 3B is a top plan view of a light blocking plate used in the inspecting system of the FIG. 3A embodiment.

FIG. 7 is a schematic and diagrammatic view of a main portion of a semiconductor device manufacturing system, as an example, which embodies a semiconductor device manufacturing method according to an embodiment of the present invention.

FIG. 8 is a schematic and diagrammatic view of a portion of a semiconductor device manufacturing system which embodies a semiconductor device manufacturing method according to another embodiment of the present invention.

DESCRIPTION OF THE PREFERRED EMBODIMENTS

Figure 2:
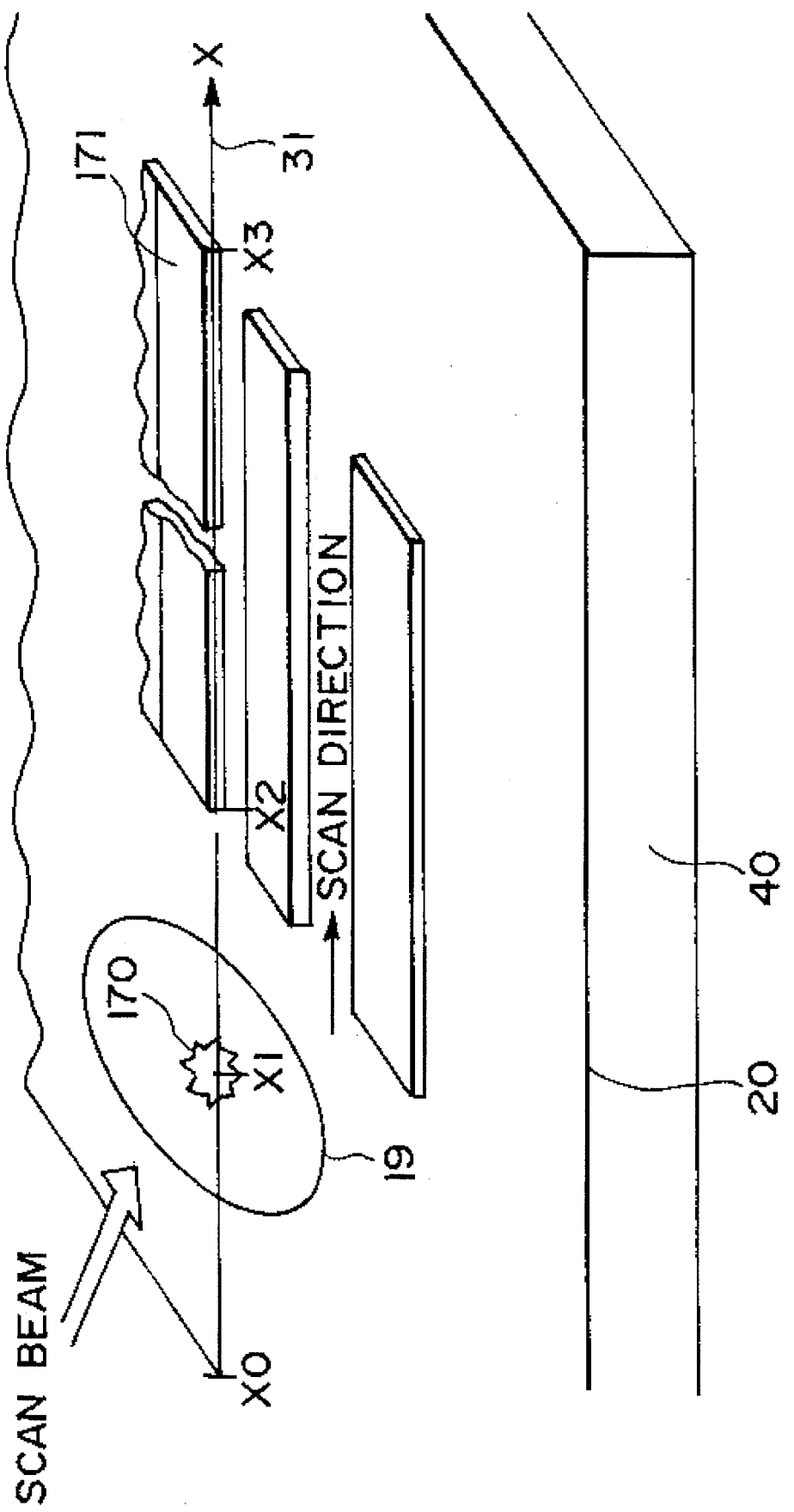
FIG. 2 is an enlarged and perspective view of a portion of the inspecting system of the FIG. 1A embodiment.

FIGS. 1A and 1B show a first embodiment of a foreign particle inspecting system of the present invention.

In this embodiment, the invention is applied to an inspecting system for inspecting the surface state of the surface of an original (reticle or photomask) or the surface of a wafer, to be used in the field of semiconductor device manufacturing, more particularly, for inspecting a foreign particle such as dust or a fault such as a scratch (hereinafter, simply, a "foreign particle"), adhered to the surface to be examined.

FIG. 1A is side view and FIG. 1B is a top plan view of a light blocking plate used in this embodiment. Denoted in these drawings at 11 is a laser light source, and denoted at 12 is a polarizer. Denoted at 13 is a filter, and denoted at 14 is a lens system. The components from the polarizer 12 to the lens system 14, inclusive, constitute a collimator optical system 2. Denoted at 17 is a scanning mirror such as a polygonal mirror, and denoted at 18 is an f-θ lens. The scanning mirror 17 and the f-θ lens 18 provide a scanning optical system 3.

Denoted at 40 is an original and denoted at 20 is the surface thereof with respect to which presence/absence of any foreign particle or fault is going to be inspected. On the surface 20, a circuit pattern is formed. Denoted at 27 is a pellicle film which serves to protect the surface of the original (the surface to be inspected). Denoted at 29 is a scanning stage system.

Denoted at 21 is a light receiving lens system, and denoted at 22 is a filter. Denoted at 23 is an aperture member, and denoted at 24 is a photoelectric detector. The components from the light receiving lens 21 to the photoelectric detector 24, inclusive, constitute detecting means 4.

Denoted at 30 is a light blocking plate which, as is best seen in FIG. 1B, has an opening 50. The light blocking plate 30 is disposed in the neighborhood of the original 40 and substantially parallel to the original 40.

In operation of the inspecting system of this embodiment, in FIG. 1A, a laser beam from the laser light source 11 is transformed by the collimator optical system 2 into a laser beam suitable for foreign particle inspection. It is then directed by a mirror 15 to the scanning optical system 3. The laser beam from the scanning optical system 3 goes through the opening 50 of the light blocking plate 30, and it is collected as a light spot 19 upon the surface 20 to be inspected, on which surface a circuit pattern is formed. By the scanning optical system, the light spot 19 scans that surface along a scan line. Simultaneously, by means of the scanning stage system 26, the original 40 is moved in a direction substantially perpendicular to the scanning direction of the light spot 19, whereby the whole surface 20 is scanned two-dimensionally.

With respect to the direction of projection of this laser beam, the detecting means 4 is disposed backwardly to receive backward scattered light. Thus, it receives backward scattered light from the light spot 19 on the surface 20, coming through the opening 50 of the light blocking plate 30.

As regards the disposition of the detecting means 4, since scattered light from a circuit pattern, for example, on the surface 20 has a particular diffraction direction or directions, it is so selected that the detecting means avoids such diffraction directions and does not receive the scattered light diffracted in those directions.

FIG. 2 is a schematic view for explaining the positional relationship among a foreign particle and a circuit pattern on the surface 20 being inspected and the light beam projected thereon. FIG. 2 shows the presence of a foreign particle 170 and a circuit pattern 171, both being present on a scan line 31 of the laser beam, in an illustration viewing the light irradiation position on the original 40 from the light projection side or from the detecting means side.

With the arrangement of the inspecting system described above, if there is no foreign particle within the range of the light spot 19, no scattered light is detected by the detecting means 4. If there is a small foreign particle such as at 170, scattered light is isotropically produced from the particle 170. Thus, the detecting means 4 detects scattered light. Inspection of the presence/absence of a foreign particle is performed by processing a detection signal, produced in response thereto, through a signal processing system 25.

With the arrangement described above, in a case when there is no foreign particle within the range of the light spot 19 and if light reflected by the surface 20, for example, impinges on the pellicle frame 28 and is scattered by that frame, reflectively scattered light such as at 29 produced thereby is blocked by the light blocking plate 30. Thus, it does not reach the detecting means 4. If, on the other hand, there is a small foreign particle, scattered light from the particle goes through the opening 50 of the light blocking plate 30 and it reaches the detecting means 4. Thus, the scattered light is detected. In this case, there also may occur reflection of light by the surface 20 being inspected. However, any scattered light produced from any portion off the scan line is effectively intercepted by the light blocking plate 30. It is therefore possible to eliminate unwanted noise light. Thus, the signal processing system 25 processes a detection signal with a reduced noise component from the detecting means 4, whereby very accurate inspection is assured.

The light blocking plate 30 is disposed adjacent to the original and substantially parallel to the original 40. Thus, it does not interfere with the motion of the scanning stage system 26 and, as a result, a larger light blocking range can be set as viewed from the detecting means 4 side.

Further, at least the surface of the light blocking plate 30, facing the surface 20 to be inspected, has been treated by a surface treatment such as a roughing treatment, a back-painting treatment or a velveting treatment, for example, so that it does not reflect light impinging thereon to produce unwanted reflected light or scattered light.

FIGS. 3A and 3B show a main portion of a second embodiment of a foreign particle inspecting system of the present invention. FIG. 3A is a side view of the inspecting system, and FIG. 3B is a top plan view of a light blocking plate of this embodiment. As compared with the first embodiment, the second embodiment differs in the point that the opening formed of the light blocking plate 30 is bisected into a scanning beam passage opening 52 and a light receiving opening 53. The remaining portion of this embodiment has substantially the same structure as that of the first embodiment.

More specifically, the light blocking plate 30 of this embodiment is formed with openings 52 and 53 which are defined only in an area through which the scanning laser beam passes and an area through which light reflected from light spots formed sequentially along the scan line 31 toward the detecting means 4 passes. The remaining area of the light blocking plate is effective to block scattered light produced in any portion off the scan line 31. Thus, the blocking effect to unwanted light is superior to that of the first embodiment.

Figure 4A:
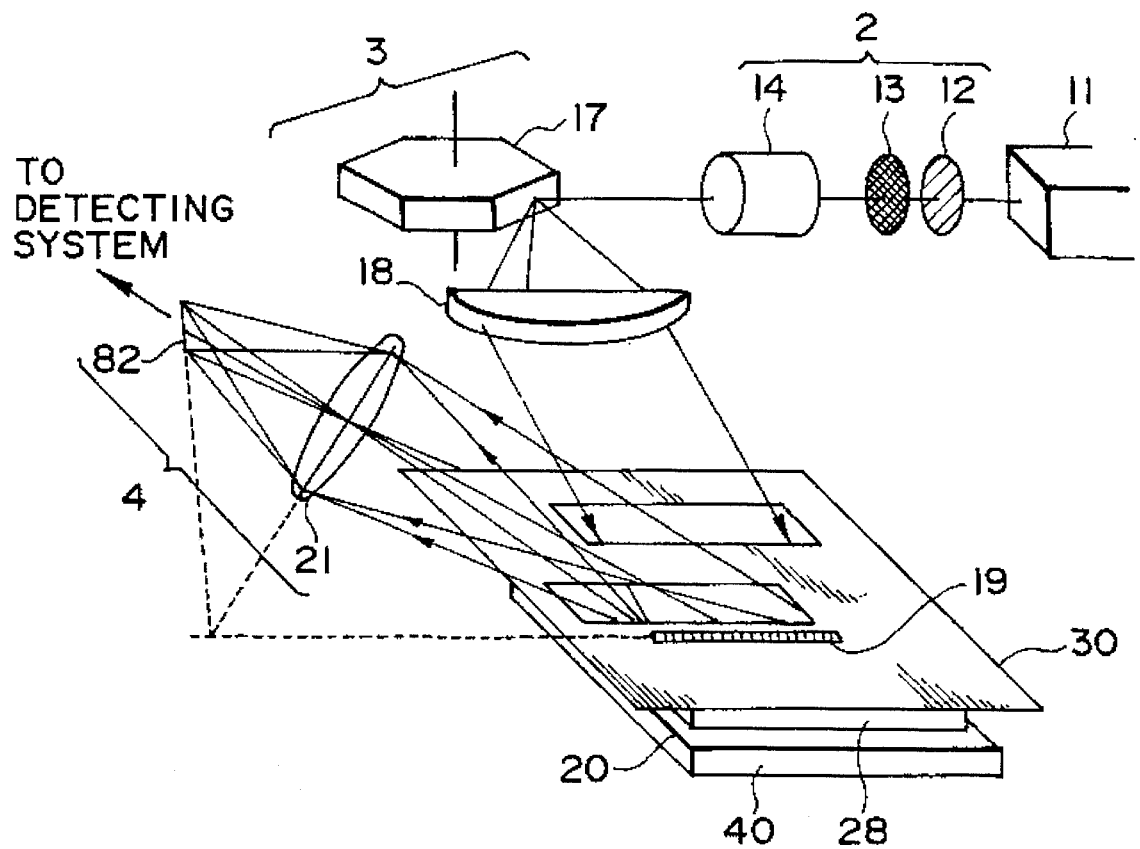
FIG. 4A is a schematic and perspective view of a main portion of a foreign particle inspecting system according to a third embodiment of the present invention.
Figure 4B:
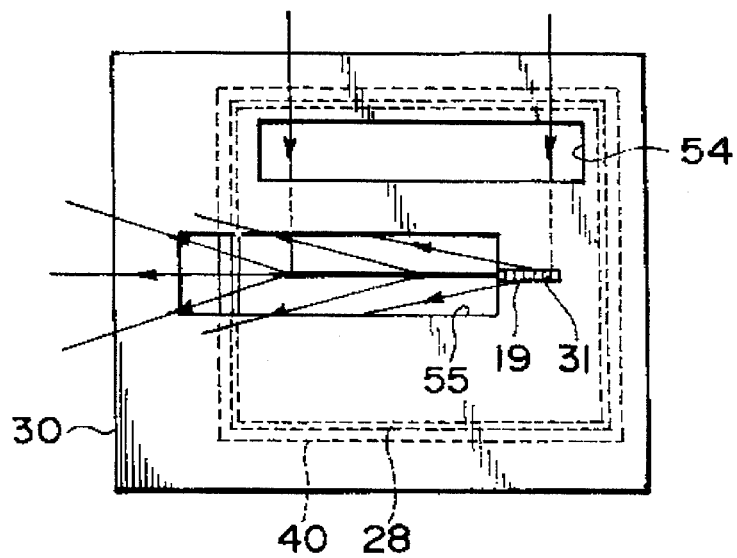
FIG. 4B is a top plan view of a light blocking plate used in the inspecting system of the FIG. 4A embodiment.

FIGS. 4A and 4B show a main portion of a third embodiment of a foreign particle inspecting system of the present invention. FIG. 4A is a schematic and perspective view of the inspecting system, and FIG. 4B is a top plan view of a light blocking plate of this embodiment.

The first and second embodiments are examples of backward light reception wherein the detecting means 4 is disposed backwardly of the scan line 31. As compared, the third embodiment is an example of sideward light reception wherein detecting means 4 is disposed along side, of the scan line 31. In FIG. 4A, a stage mechanism for moving the surface 20 to be inspected relative to the scan line 31 and a portion of the detecting means 40 are omitted.

In this embodiment, the detecting means is disposed sidewardly with respect to the direction of projection of the laser beam to the surface 20 to be inspected. The detecting means 4 receives only the scattered light from each light spot on the surface 20 coming through a light receiving opening 55 formed in the light blocking plate 30. Since scattered light produced by a circuit pattern, for example, formed on the surface 20 has a particular diffraction direction or directions, disposition of the detecting means 4 is so selected to avoid such directions, such that the detecting means does not receive the diffraction light from the circuit pattern.

With the arrangement described above, in a case when there is no foreign particle within the range of the light spot 19 and if light reflected by the surface 20, for example, impinges on the pellicle frame 28 and is scattered by that frame, irregularly reflected light such as at 29 produced thereby is blocked by the light blocking plate 30. Thus, it does not reach the detecting means 4. If, on the other hand, there is a small foreign particle, scattered light from the particle goes through the light receiving opening 55 of the light blocking plate 30 and it reaches the detecting means 4. Thus, the scattered light is detected. In this case, there also may occur reflection of light by the surface 20 being inspected. However, any scattered light produced from any portion off the scan line is effectively intercepted by the light blocking plate 30. It is therefore possible to eliminate unwanted noise light. Thus, the signal processing system 25 processes a detection signal with a reduced noise component from the detecting means 4, whereby very accurate inspection is assured.

Figure 5A:
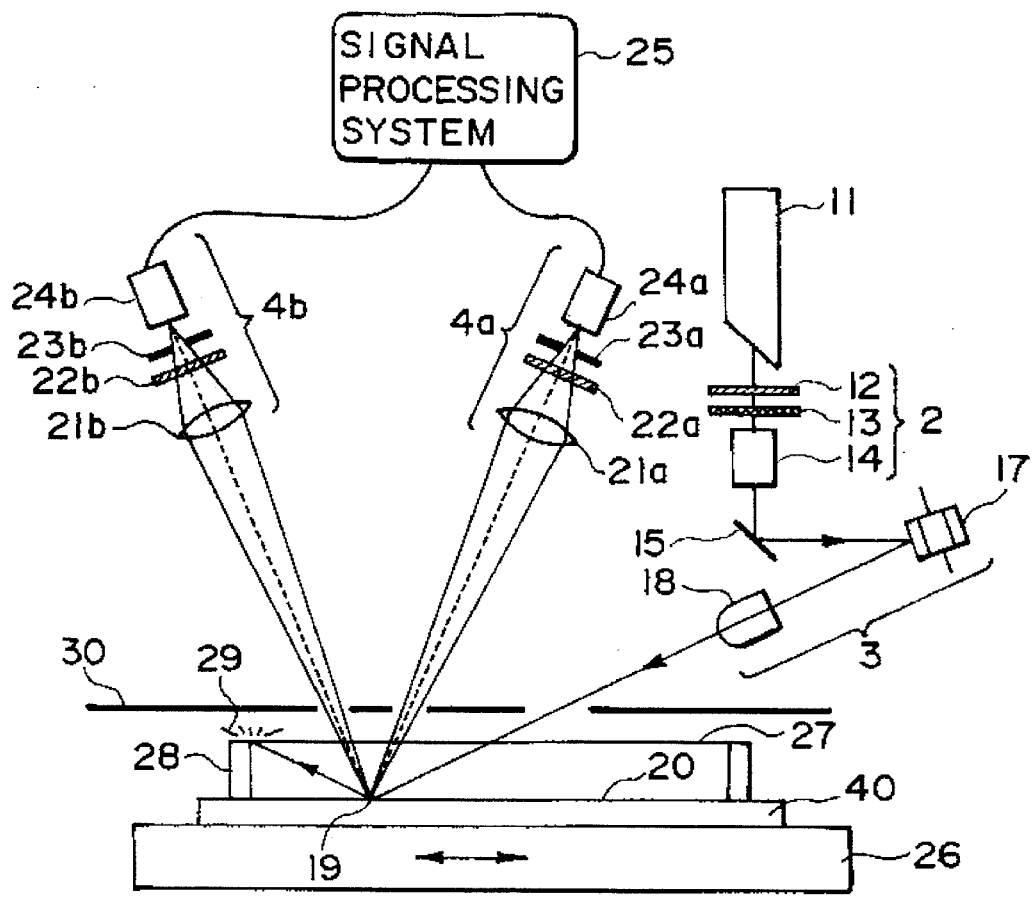
FIG. 5A is a schematic and side view of a main portion of a foreign particle inspecting system according to a fourth embodiment of the present invention.
Figure 5B:
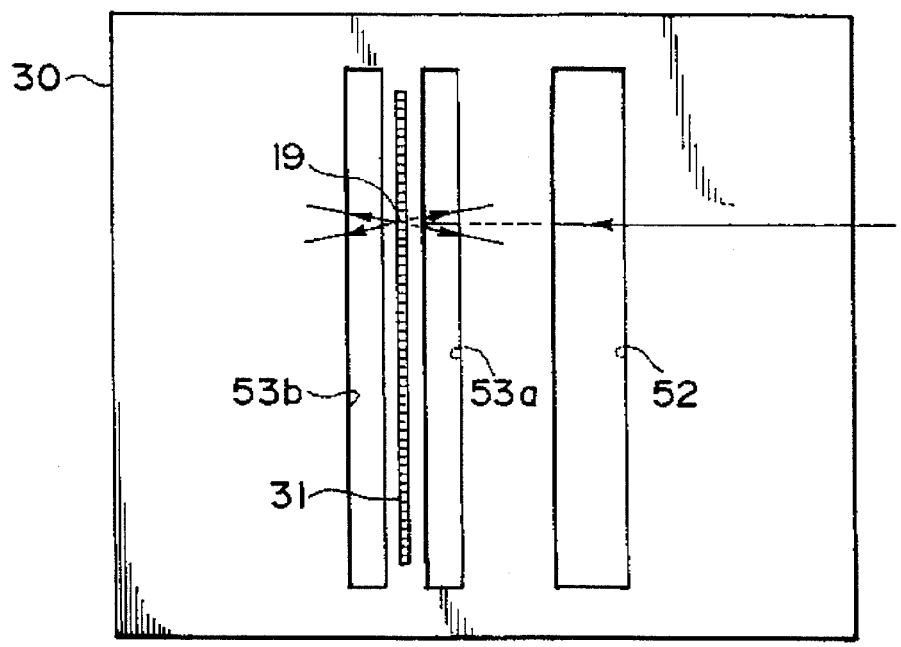
FIG. 5B is a top plan view of a light blocking plate used in the inspecting system of the FIG. 5A embodiment.

FIGS. 5A and 5B show a main portion of a fourth embodiment of a foreign particle inspecting system of the present invention. FIG. 5A is a schematic and side view of the inspecting system, and FIG. 5B is a top plan view of a light blocking plate of this embodiment.

The first to third embodiments are examples wherein inspection is performed by using a single detecting means (4). As compared, the fourth embodiment is an example wherein two detecting means 4a and 4b are used to perform the inspection with respect to two azimuth angles. The fourth embodiment differs from the second embodiment of FIG. 3A in the points that two detecting means 4 are used and that the light blocking plate 30 is provided with two openings, i.e., an opening 53a and an opening 53b. The remaining portion of this embodiment has substantially the same structure as that of the second embodiment.

With the arrangement described above, in a case when there is no foreign particle within the range of the light spot 19 and if light reflected by the surface 20, for example, impinges on the pellicle frame 28 and is scattered by that frame, irregularly reflected light such as at 29 produced thereby is blocked by the light blocking plate 30. Thus, it does not reach the detecting means 4a or 4b. If, on the other hand, there is a small foreign particle, scattered light from the particle goes through the light receiving opening 53a or 53b of the light blocking plate 30 and it reaches the detecting means 4a or 4b. Thus, the scattered light is detected. In this case, there also may occur reflection of light by the surface 20 being inspected. However, any scattered light produced from any portion off the scan line is effectively intercepted by the light blocking plate 30. It is therefore possible to eliminate unwanted noise light. Thus, the signal processing system 25 processes a detection signal with a reduced noise component from the detecting means 4, whereby very accurate inspection is assured.

In this embodiment, two detecting means 4 are used. However, three or more detecting means may be used and, on that occasion, the light blocking plate 30 may similarly be provided with openings of the number corresponding to that of the detecting means 4 to intercept scattered light from any portion off the scan line region. Further, if plural detecting means 4 have detection angles being close to each other, light receiving openings of a number smaller than the number of the detecting means may be used to detect the necessary scattered light only.

As an alternative, a plurality of laser beams may be projected onto the surface 20 to be inspected. On that occasion, the light blocking plate 30 may be provided with scanning beam openings corresponding to those scanning light beams, respectively, as well as a light receiving opening or openings. Unwanted scattered light can be eliminated with such a structure.

Figure 6A:
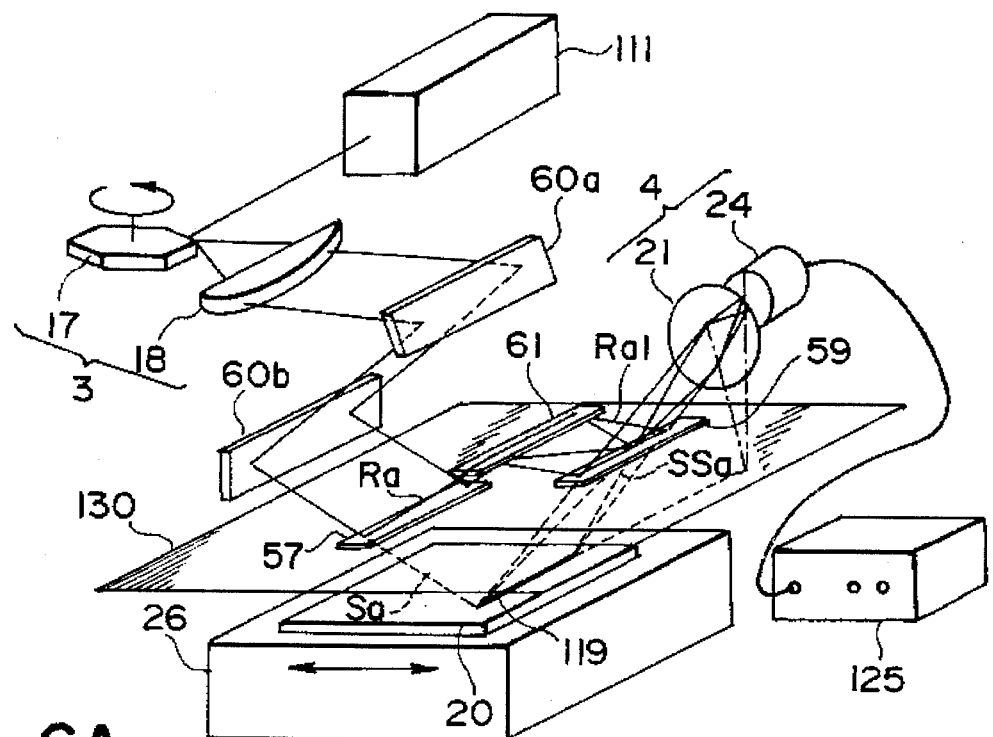
FIG. 6A is a schematic and perspective view of a main portion of a foreign particle inspecting system according to a fifth embodiment of the present invention.
Figure 6B:
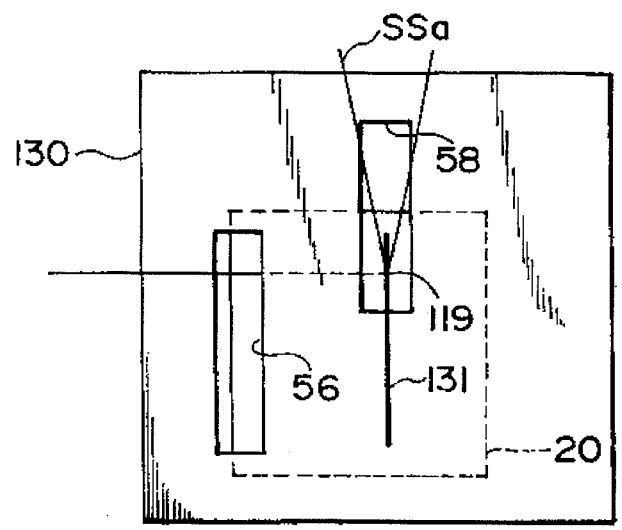
FIG. 6B is a top plan view of a light blocking plate used in the inspecting system of the FIG. 6A embodiment.
Figure 6C:
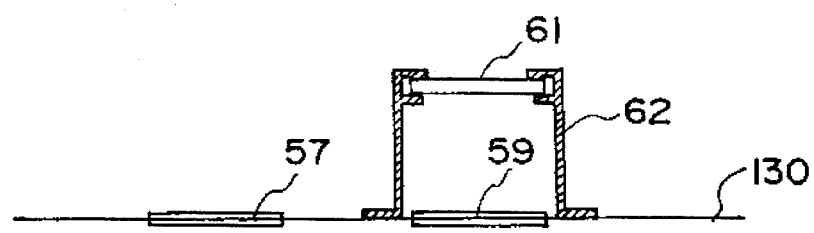
FIG. 6C is a side view of the light blocking plate of FIG. 6B.
Figure 9:
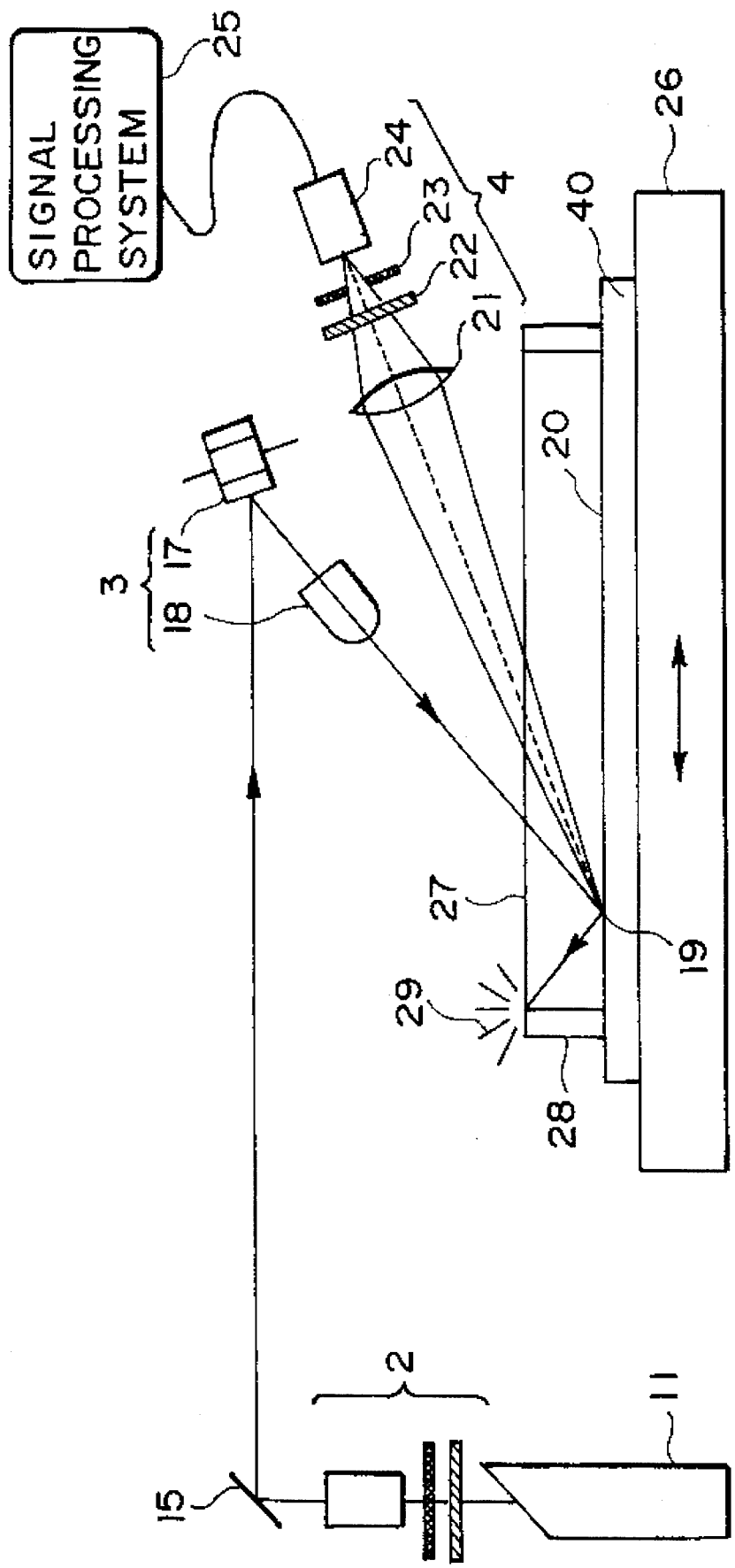
FIG. 9 is a schematic and side view for explaining a general concept of a foreign particle inspecting system.

FIGS. 6A–6C show a main portion of a fifth embodiment of a foreign particle inspecting system of the present invention. FIG. 6A is a perspective view of the inspecting system, FIG. 6B is a top plan view of a light blocking plate of this embodiment, and FIG. 6C is a side view of the light blocking plate. In this embodiment, particle inspection is based on heterodyne interference of two light beams.

Denoted in the drawing at 111 is a laser light source which comprises, in this example, a dual-frequency orthogonal laser for providing a laser beam of two components having slightly different frequencies and having different polarization planes intersecting perpendicular to each other. Denoted at 130 is a light blocking plate. Denoted at 56 is a scanning beam passage opening, and denoted at 58 is a light receiving opening. Disposed at the scanning beam passage opening 56 is a polarization beam splitter 57, and disposed at the light receiving opening 58 is a wave combining mirror 59. This wave combining mirror 59 comprises a half mirror and a polarization beam splitter, for example. The polarization beam splitter 57 and the wave combining mirror 59 each is an optical component provided at the opening. Denoted at 61 is a grating which functions to produce reflectively scattered light sidewardly with respect to the light incident thereon.

The light beam emitted by the light source 111 is deflected by a scanning optical system 3 which comprises a polygonal mirror 17 and an f-θ lens 18. By way of mirrors 60a and 60b, the light finally passes the opening 56 of the light blocking plate 130, whereby a light spot 119 is formed on the surface 20 to be inspected, and scanning is done along a scan line 131.

Here, since the polarization beam splitter 57 is positioned at the scanning beam passage opening 56 of the light blocking plate 130, the light beams of two frequencies of the light flux are separated into two polarized light beams of the respective frequencies, such that an inspection beam Sa for scanning the surface 20 and a reference beam Ra directed to the diffraction grating 61 are produced.

Detecting means 4 is disposed sidewardly of the scan line 131, and only scattered light from the light spot 119 on the surface 20 being inspected is received thereby through the light receiving opening 58 of the light blocking plate 130.

On the other hand, the reference beam Ra is diffracted by the diffraction grating 61. First order diffraction light of the diffracted light is being diffracted toward the light receiving opening 58. Since the wave combining mirror 59 is provided at the light receiving opening 58, the measurement light SSa which is sideward scattered light from a particle on the surface 20 and the reference light Ra1 which is diffraction light from the diffraction grating are superposed one upon another by the wave combining mirror 59. The combined light is directed to the detecting means 4. The measurement light SSa and the reference light Ra1 are photoelectrically converted by the detecting means 4 and detected thereby as an interference signal. Since the two lights have a small difference in frequency, this signal is detected as a modulation signal of differential frequency.

With the arrangement described above, in a case when there is no foreign particle within the range of the light spot 119 and if light reflected by the surface 20, for example, impinges on the pellicle frame 28 and is scattered by that frame, irregularly reflected light such as at 129 produced thereby is blocked by the light blocking plate 130. Thus, it does not reach the photodetector 24. If, on the other hand, there is a small foreign particle, scattered light from the particle is combined with the reference light by means of the wave combining mirror 59 disposed at the light receiving opening 58 of the light blocking plate 130, and it reaches the detecting means 4. Thus, the scattered light is detected as an interference signal. In this case, there also may occur reflection of light by the surface 20 being inspected. However, any scattered light produced from any portion off the scan line 131 is effectively intercepted by the light blocking plate 130. It is therefore possible to eliminate unwanted noise light. Thus, the signal processing system 125 processes a detection signal with a reduced noise component from the detecting means 4, whereby very accurate inspection is assured.

In this embodiment, the light blocking plate 130 is disposed substantially parallel to the surface 20 to be inspected. This is particularly convenient for placing optical components such as the polarization beam splitter 57 or the wave combining mirror 59, for example.

The grating 61 can be easily placed parallel to the surface 20, this being able to be done by fixing the grating 61 to the light blocking plate 130 through a holder 62 parallel to the light blocking plate 130, as shown in FIG. 6C, and finally, by adjusting the light blocking plate to be parallel to the surface to be inspected.

Further, at least the surface of the light blocking plate 130 facing the surface 20 to be inspected may be treated by a surface treatment such as a roughing treatment, a backpainting treatment or a velveting treatment, for example, so that it does not reflect light impinging thereon to produce unwanted reflected light or scattered light.

The light blocking plate 130 of this embodiment serves to intercept and prevent unwanted scattered light, produced at the detecting means 4 side of the light blocking plate 4 from reaching the surface 20 side and, additionally, it serves to block and prevent unwanted scattered light, produced between the light blocking plate 130 and the original 10 from reaching the detecting means 4.

In the first to fifth embodiments, the scanning optical system 3 uses a polygonal mirror. However, similar advantageous results are attainable with a scanning optical system 3 which uses an oscillation mirror such as a galvano mirror. Further, similar advantageous results are attainable with a system wherein, without oscillating a projected beam, the surface to be inspected is scanned relative to the optical system.

An an occasion when a light beam is projected to the original 40 from the back side where no detecting means is disposed, a light blocking plate substantially parallel to the original 40 may be disposed between the original 40 and the detecting means. Unwanted scattered light may be then blocked by providing the light blocking plate with a light receiving opening only.

It is to be noted that the applicability of the embodiments described above is not limited to the field of semiconductor manufacture. They also may be applied widely to an inspecting system for inspection of surface state.

FIG. 7 is a schematic view for explaining an embodiment of a semiconductor device manufacturing method of the present invention. In this embodiment, a foreign particle inspecting system according to any one of the embodiments described above is incorporated into a manufacturing system for manufacturing semiconductor devices by printing a circuit pattern of an original such as a reticle or photomask on a wafer. The system generally comprises an exposure apparatus, an original accommodating device, an original inspecting device (foreign particle inspecting device) and a controller. These components are housed in a clean room.

Denoted in FIG. 7 at 901 is a deep ultraviolet light source such as an excimer laser, and denoted at 902 is a unit illumination system. By means of these components, an original 903 as placed at the exposure position EP is illuminated from above, simultaneously with a predetermined numerical aperture (N.A.). Denoted at 909 is a projection lens for projecting and printing a circuit pattern of the original 903 onto a wafer 910 such as a silicon substrate, for example. In the projection printing procedure, an exposure process is repeated while shifting the wafer 910 step by step (shot by shot) in accordance with the stepwise motion of a movable stage 911. Denoted at 900 is an alignment system for aligning the original 903 and the wafer 910 with each other, prior to the exposure process. The alignment system 900 comprises at least one original observing microscope system.

The above-described components are constituent elements of the exposure apparatus.

Denoted at 914 is an original accommodating device for accommodating plural originals therein. Denoted at 913 is an inspecting device (foreign particle inspecting device) for detecting the presence/absence of a foreign particle on an original. This inspecting device has a structure as has been described with reference to any one of the preceding embodiments. The inspecting device 913 performs inspection of any foreign particle or particles on an original after it is taken out of the accommodating device 9 and before it is placed at the exposure position EP.

The principle and operation of the particle inspection are the same as those of any one of the preceding embodiments. The controller 918 controls the overall sequence of the manufacturing system as a whole. Specifically, it controls the operations of the accommodating device 914 and the inspecting device 913 as well as the alignment operation, the exposure operation and the wafer stepwise feeding motion which are basic operations of the exposure apparatus.

Next, semiconductor device manufacturing processes to be made through this manufacturing system will be explained.

First, an original 903 to be used is taken out of the accommodating device 914. It is placed into the inspecting device 913.

After this, foreign particle inspection is done, in the inspecting device 914, to the original 903. If an absence of a particle is discriminated as a result of the inspection, the inspected original is moved to the exposure position EP within the exposure apparatus.

Subsequently, a semiconductor wafer 910 which is a workpiece to be exposed is placed on the movable stage 911. Then, while moving the wafer shot by shot with the stepwise feeding of the movable stage 911 in accordance with the step-and-repeat method, the pattern of the original is projected and printed onto each zone of the semiconductor wafer 910 in a reduced scale. This operation is repeated.

When exposure of the whole surface of one semiconductor wafer 910 is completed, it is unloaded and a subsequent semiconductor wafer is loaded. In a similar manner, printing of the pattern of the original is performed in the step-and-repeat method.

An exposed wafer or wafers having been treated by the exposure process are then treated by predetermined known procedures such as a developing process and an etching process, for example. Then, through an assembling procedure such as dicing, wire bonding and packaging, for example, semiconductor devices are manufactured.

FIG. 8 is a block diagram of a portion of a second embodiment of a semiconductor device manufacturing method of the present invention. In this embodiment, a foreign particle inspecting system according to any one of the preceding embodiments is incorporated into a cleaning and inspecting system for an original such as a reticle or photomask, to be used in the manufacture of semiconductor devices. The cleaning and inspecting system constitutes one portion of the semiconductor device manufacturing system.

The cleaning and inspecting system generally comprises an original accommodating device, a cleaning device, a dryer device, an inspecting device (foreign particle inspecting device) and a controller, and these components are housed in a clean chamber.

Denoted in FIG. 8 at 920 is an original accommodating device for accommodating plural originals therein and for supplying originals to be cleaned. Denoted at 921 is a cleaning device for cleaning or washing an original with pure water. Denoted at 922 is a dryer device for drying a cleaned original. Denoted at 923 is an inspecting device (foreign particle inspecting device) which has a structure the same as that of any one of the preceding embodiments, for performing particle inspection to a cleaned original. Denoted at 924 is a controller for controlling the overall sequence of the cleaning and inspecting system as a whole.

In operation, first an original to be cleaned is taken out of the accommodating device 920 and it is fed into the cleaning device 921. The original cleaned by the cleaning device 921 is moved into the dryer device 922, whereby it is dried. After drying, the original is fed into the inspecting device 923, by which, inspection of a foreign particle on the original is performed in accordance with the method described with reference to any one of the preceding embodiments.

If no particle is found as a result of the inspection, the original is moved back into the accommodating device 920. If a particle or particles are found, then this original is fed back to the cleaning device 921 whereby the cleaning operation is repeated. After the drying operation through the dryer device 922, the original is inspected again by the inspecting device 923. This operation is repeated until all particles on the original are completely removed. A completely clean original is then moved back into the accommodating device 920.

Subsequently, a cleaned original is loaded into the exposure apparatus, and a circuit pattern of the original is printed on a semiconductor wafer for manufacture of semiconductor devices.

While the invention has been described with reference to the structures disclosed herein, it is not confined to the details set forth and this application is intended to cover such modifications or changes as may come within the purposes of the improvements or the scope of the following claims.

What is claimed is:

1. An inspecting system, comprising:

a light source;

an irradiating optical system for irradiating a surface of an object with light from said light source;

a detection optical system for detecting scattered light from the surface of the object; and light blocking means provided substantially parallel to the surface of the object, said light blocking means having a first light transmitting portion for passing light coming from said light source toward the surface of the object and a second light transmitting portion for passing light coming from an irradiated position on the surface of the object toward said detection optical system, said light blocking means having a surface, facing the surface of the object, having been processed by a reflection reducing treatment.

2. A system according to claim 1, wherein said irradiating optical system comprises a scanning optical system for scanning the surface of the object with light.

3. A system according to claim 1, wherein said light blocking means comprises a light blocking plate and wherein said first and second light transmitting portions each comprises an opening formed in said light blocking plate.

4. A system according to claim 3, wherein said light blocking plate has a surface, facing the surface of the object, having been treated by an anti-reflection treatment.

5. An inspecting system, comprising:

a light source;

an irradiating optical system for irradiating a surface of an object with light from said light source;

a detection optical system for detecting scattered light from the surface of the object;

light blocking means provided substantially parallel to the surface of the object, said light blocking means having a first light transmitting portion for passing light coming from said light source toward the surface of the object and a second light transmitting portion for passing light coming from an irradiated position on the surface of the object toward said detection optical system; and exposure means for exposing the object having been inspected by said inspecting system.

6. An inspecting system, comprising:

a light source;

an irradiating optical system for irradiating a surface of an object with light from said light source;

a detection optical system for detecting scattered light from the surface of the object;

light blocking means provided substantially parallel to the surface of the object, said light blocking means having a first light transmitting portion for passing light coming from said light source toward the surface of the object and a second light transmitting portion for passing light coming from an irradiated position on the surface of the object toward said detection optical system; and cleaning means for cleaning the object having been inspected by said inspecting system.

7. A system according to claim 5, wherein the object comprises one of an original having a pattern to be transferred and a wafer.

8. A system according to claim 6, wherein the object comprises one of an original having a pattern to be transferred and a wafer.

9. A system according to claim 3, wherein said first light transmitting portion and said second light transmitting portion are defined by one and the same opening formed in said light blocking plate.

10. A system according to claim 3, wherein said first light transmitting portion and said second light transmitting portion are defined by different openings formed in said light blocking plate.

* * * * *

UNITED STATES PATENT AND TRADEMARK OFFICE
CERTIFICATE OF CORRECTION

PATENT NO. : 5,585,918
DATED : December 17, 1996
INVENTOR(S) : Seiji TAKEUCHI, et al.

It is certified that error appears in the above-indentified patent and that said Letters Patent is hereby corrected as shown below:

COLUMN 8:

Line 17, "An" should read --On--.

Signed and Sealed this

Twenty-ninth Day of April, 1997

Attest:

BRUCE LEHMAN

*Attesting Officer*     *Commissioner of Patents and Trademarks*